(12) United States Patent
Montagnoni et al.

(10) Patent No.: US 9,645,047 B2
(45) Date of Patent: May 9, 2017

(54) METHOD AND APPARATUS FOR MEASUREMENT OF THE NOISINESS OF A ROLLING BEARING, IN PARTICULAR OF A WHEEL HUB BEARING UNIT

(71) Applicants: Raffaele Montagnoni, Pinerolo (IT); Luca Volpato, Turin (IT)

(72) Inventors: Raffaele Montagnoni, Pinerolo (IT); Luca Volpato, Turin (IT)

(73) Assignee: AKTIEBOLAGET SKF, Gothenburg (SE)

( * ) Notice: Subject to any disclaimer, the term of this patent is extended or adjusted under 35 U.S.C. 154(b) by 281 days.

(21) Appl. No.: 14/394,439

(22) PCT Filed: Apr. 11, 2013

(86) PCT No.: PCT/IB2013/000654
§ 371 (c)(1),
(2) Date: Oct. 14, 2014

(87) PCT Pub. No.: WO2013/153434
PCT Pub. Date: Oct. 17, 2013

(65) Prior Publication Data
US 2015/0219526 A1   Aug. 6, 2015

(30) Foreign Application Priority Data

Apr. 13, 2012   (IT) .............................. TO2012A0323

(51) Int. Cl.
*G01N 29/22* (2006.01)
*G01N 15/00* (2006.01)
(Continued)

(52) U.S. Cl.
CPC .......... *G01M 13/045* (2013.01); *G01N 29/22* (2013.01); *G01N 29/44* (2013.01); *G01P 1/023* (2013.01); *G01P 15/00* (2013.01)

(58) Field of Classification Search
CPC ...... G01M 13/045; G01P 15/00; G01P 1/023; G01N 29/22; G01N 29/44
(Continued)

(56) References Cited

U.S. PATENT DOCUMENTS 3,456,484 A * 7/1969 Schwartz .............. G01M 7/025
                                                73/1.82
3,911,731 A * 10/1975 Walker ................... G01M 1/02
                                                73/660

(Continued)

FOREIGN PATENT DOCUMENTS

JP    20070247826    * 9/2007
WO   WO2008128364   * 10/2008

*Primary Examiner* — J M Saint Surin
(74) *Attorney, Agent, or Firm* — Bryan Peckjian; SKF USA Inc. Patent Dept.

(57) ABSTRACT

A method wherein the possible abnormal noisiness and vibrations of a rolling bearing for a wheel hub unit are detected by fixing a first one of the inner and outer rings of the bearing integral on a support provided with a first and a second accelerometer so that the first and second accelerometers have respective measurement axes (X, Y) arranged at a right angle relative to each other on a plane perpendicular to the axis of symmetry (A) of the bearing. A second ring of the bearing is angularly coupled with means for rotating it at a predetermined speed, calculated beforehand based on operating parameters of the bearing; processing means detect in a predetermined time interval a first and a second electric signal (T1, T2) emitted by the first and second accelerometers and, through a frequency analysis, obtain a frequency spectrum (P) of the amplitude of any vibrations detected.

9 Claims, 4 Drawing Sheets (51) Int. Cl.
  *G01P 1/02* (2006.01)
  *G01N 29/44* (2006.01)
  *G01M 13/04* (2006.01)
  *G01P 15/00* (2006.01)

(58) Field of Classification Search
  USPC .......................................................... 73/593
  See application file for complete search history.

(56) References Cited

U.S. PATENT DOCUMENTS

| | | | | |
|---|---|---|---|---|
| 4,213,346 | A | * | 7/1980 | Polovnikov ......... G01M 13/028 702/113 |
| 5,423,218 | A | * | 6/1995 | Matsuzaki .......... G01M 13/045 73/593 |
| 6,034,531 | A | * | 3/2000 | Senglat .............. G01R 31/3275 324/699 |
| 6,293,151 | B1 | * | 9/2001 | Kawamata .......... G01M 13/045 73/593 |
| 7,107,850 | B2 | * | 9/2006 | Maeda .................. F16C 19/527 384/513 |
| 7,667,827 | B2 | * | 2/2010 | Nelson ..................... G01H 9/00 356/32 |
| 2008/0033695 | A1 | * | 2/2008 | Sahara ................... G01H 1/003 702/185 |
| 2008/0240642 | A1 | * | 10/2008 | Harada .............. B60B 27/0005 384/589 |
| 2013/0301968 | A1 | * | 11/2013 | Mori .................... F16C 19/186 384/456 |

\* cited by examiner

METHOD AND APPARATUS FOR MEASUREMENT OF THE NOISINESS OF A ROLLING BEARING, IN PARTICULAR OF A WHEEL HUB BEARING UNIT

CROSS REFERENCE TO RELATED APPLICATION

This is a National Stage application claiming the benefit of International Application Number PCT/IB2013/000654 filed on 11 Apr. 2013, which claims priority to Italian Patent Application No. TO2012A000323 filed on 13 Apr. 2012, both of which are herein incorporated by reference in their entirety.

FIELD OF THE INVENTION

The present invention relates to an apparatus and method for measurement of the noisiness and vibrations of a rolling bearing.

BACKGROUND OF THE INVENTION

In particular, the present invention applies to a wheel hub unit of the type comprising an inner ring and an outer ring rotatable with respect to each other due to the interposition of one or more crowns of rolling bodies, and either the inner ring or the outer ring of which may be provided with a respective flange for the connection to a wheel or to an upright according to the type of application.

Noisiness and vibrations may occur in use in the above-mentioned wheel hub units due to wear or defects of one of the components. If such noisiness and vibrations occur prematurely, e.g. when the vehicle to which they are mounted is still under guarantee, upon the replacement of the wheel hub unit the vehicle's manufacturer sends the replaced unit to the manufacturer as defective unit. The manufacturer of the wheel hub unit must therefore check whether the defects reported are actually present, and such a check currently involves not only rather considerable times and costs but, in some wheel hub units, it may be necessary to destroy the unit itself and simply disassemble it.

Moreover, the experience in the field has proved that not all the wheel hub units returned by the vehicle's manufacturer as being defective are actually such. This may happen either because the service center carries out a wrong replacement since the noise and vibrations detected by the user do not come from the unit but from another source, such as for example the tire, or because since it is not possible to positively determine which of the two units of the same axle must be replaced, the service center replaces both of them.

It is apparent that the situation described involves costs for the manufacturer of rolling bearings, which costs could be avoided if it were possible to determine the actually defective bearings without the need for disassembly operations which, in some cases, are also destructive for some components. Moreover, if the vehicle's manufacturer were able to immediately detect the rolling bearings that emit abnormal noisiness and vibrations among those replaced by the service centers, he would avoid the costs and burdens related to the return of bearings/units deemed defective to the supplier of such bearings/wheel hub units.

SUMMARY OF THE INVENTION

The object of the present invention is thus to provide a method and apparatus for quickly, efficiently and cost-effectively identifying a rolling bearing, and in particular a wheel hub unit, which emits abnormal noisiness and vibrations, so as to ensure the possibility of carrying out a first selection of the bearings/wheel hub units returned from the "field", i.e. upon on-vehicle replacement, which prevents non-defective bearings from being analyzed.

A method is thus provided according to the invention for measuring the noisiness and vibrations of a rolling bearing, and in particular of a wheel hub unit, as defined in claim 7.

An apparatus is further provided for measuring the noisiness and vibrations of a rolling bearing, and in particular of a wheel hub unit, as defined in claim 1.

BRIEF DESCRIPTION OF THE FIGURES

Features and advantages of the present invention will become apparent from the following description of a non-limiting embodiment thereof, with reference to the figures in the accompanying drawings, in which.

DETAILED DESCRIPTION OF THE INVENTION

Figure 1:
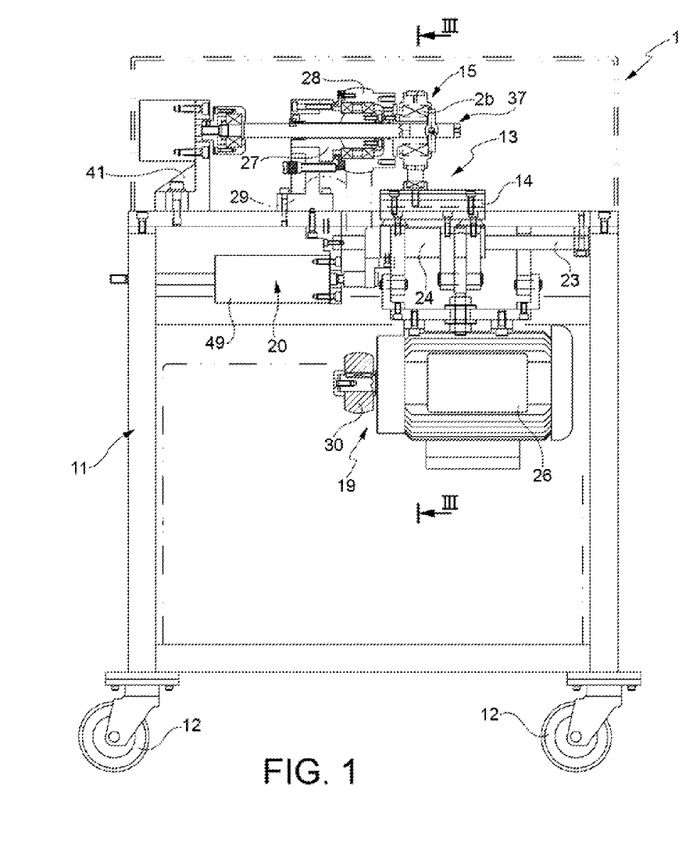
FIGS. 1 and 2 diagrammatically show front and side elevation views, respectively, of a measurement apparatus provided according to the invention equipped with two possible different fixtures.
Figure 2:
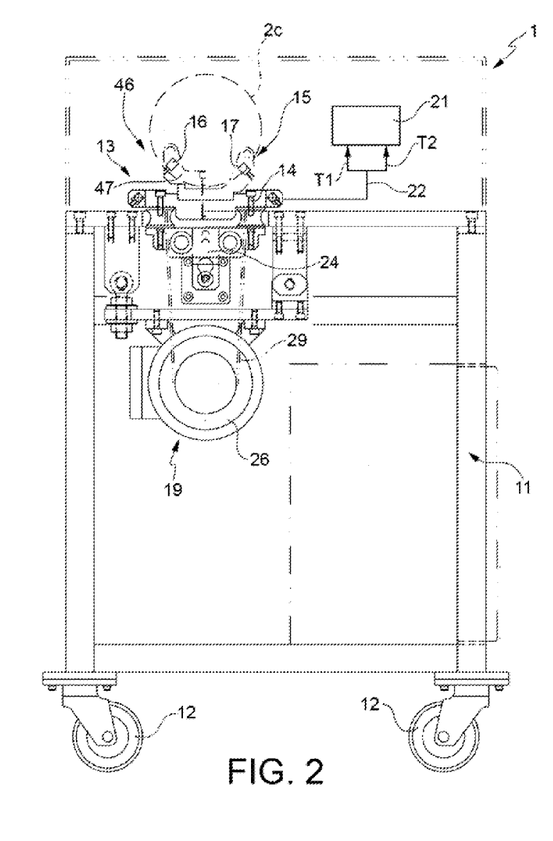
Figure 3:
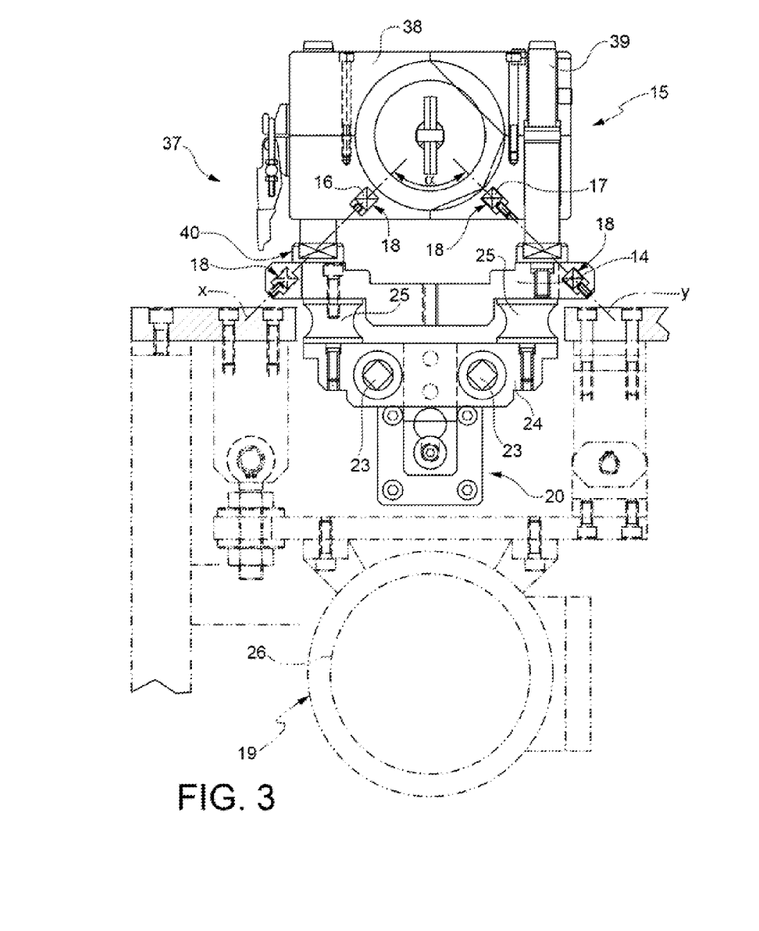
FIG. 3 diagrammatically shows an enlarged scale, section view taken according to a plotting plane III-III of a detail of a fixture of the apparatus in FIG. 1.
Figure 4:
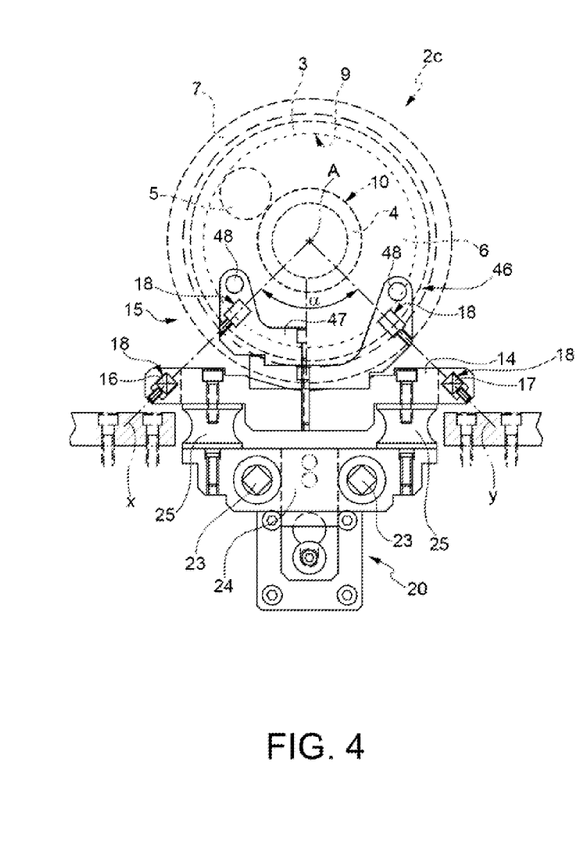
FIG. 4 diagrammatically shows a partly section view, on enlarged scale, of the same detail in FIG. 3 but of the fixture present on the measurement apparatus shown in FIG. 2.
Figures 5, 7:
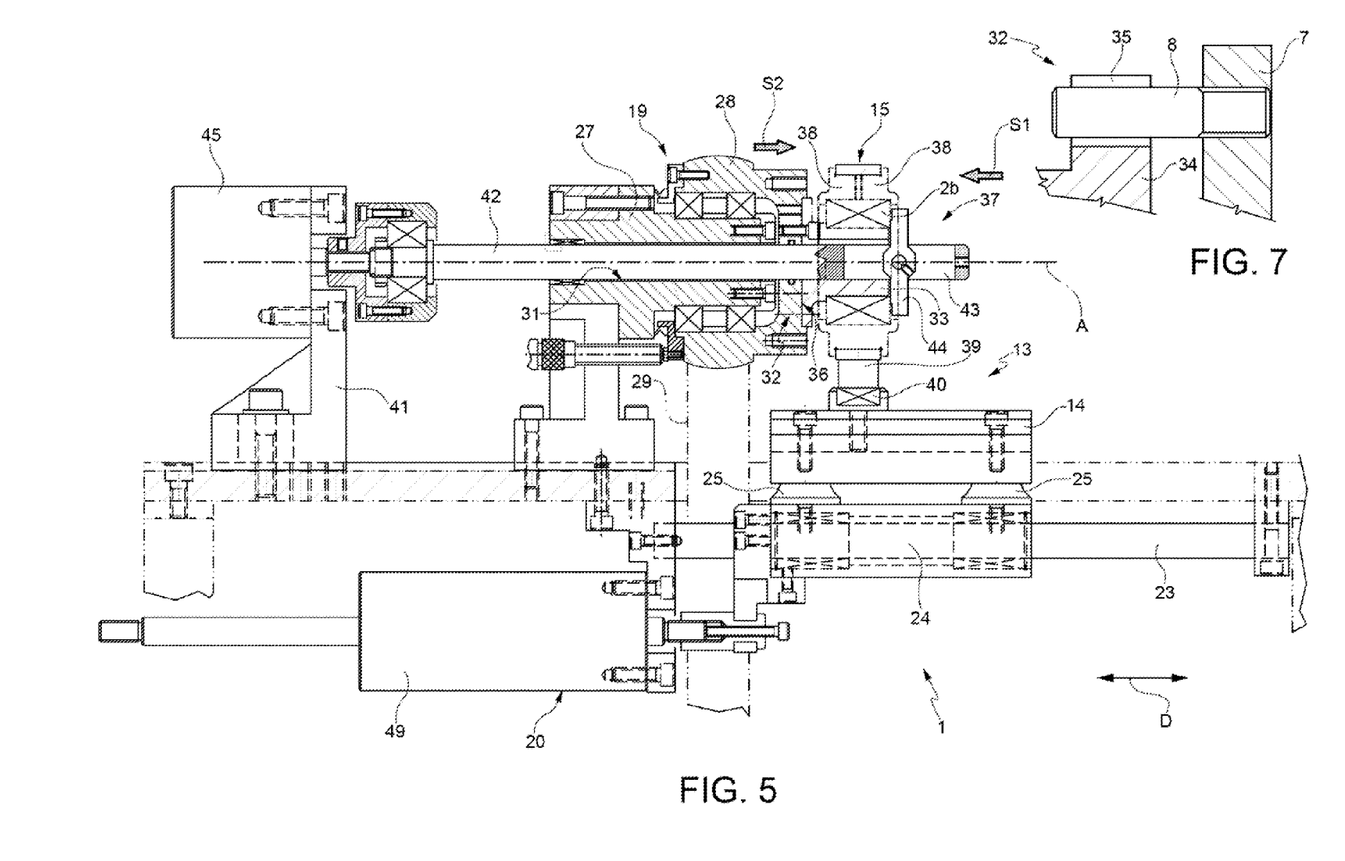
FIG. 5 shows a partly longitudinal section, diagrammatic, front view (on enlarged scale) of a detail of the apparatus in FIG. 1.
FIG. 7 shows a diagrammatic longitudinal section view, on enlarged scale, of a detail in FIG. 5, in which another different fixture is installed on the apparatus of the invention.

With reference to FIGS. 1 to 5, reference numeral 1 indicates as a whole an apparatus for measuring the noisiness and vibrations of a rolling bearing 2 of any known type; in particular, FIGS. 1 and 5 diagrammatically show a bearing 2b as a block, while a bearing 2c is diagrammatically shown with a dashed line in FIGS. 2 and 4.

Bearing 2c comprises a radially outer ring 3 and a radially inner ring 4 mounted coaxial to each other with respect to a common axis of symmetry A and between which at least one crown of rolling bodies 5 is arranged.

In particular, the bearing 2c shown forms a wheel hub unit of the known type, in which the outer ring 3 is provided with a flange 6 at an axial end thereof, and in which the inner ring 4 is optionally provided with a flange 7 at an end thereof opposite to flange 6, which flange 7 is usually provided with fastening means 8 (FIG. 7), consisting of a plurality of stud bolts peripherally arranged as a crown on flange 7, on an opposite side of flange 6.

In use, the outer ring 3 is the stationary ring of bearing 2c and is integrally fixed, in a known manner, to an upright of a vehicle suspension (known and not shown for simplicity); on the other hand, the inner ring 4 is, in use, the relatively movable ring of bearing 2c and, if it is provided with flange 7, it actually replaces the standard hub or axle present in the wheel assembly, for which bearing 2c is intended; in this case, the stud bolts 8 serve for constraining a wheel of the vehicle (not shown) directly to flange 7.

Vice versa, bearing 2b is a standard bearing provided with a radially outer ring (not shown) similar to ring 3, and with a radially inner ring (not shown) similar to ring 4, mounted coaxial to each other with respect to a common axis of symmetry A and between which at least one crown of rolling bodies (also not shown for simplicity) is arranged.

In the case of bearing 2c, two crowns of rolling bodies 5 (balls and/or rollers) are arranged between rings 3 and 4, at each one of which a surface defect may be present, which in use may produce abnormal noisiness and vibrations of bearing 2c.

From an analysis carried out on defective units returned from the "field", defects may be related to rolling tracks 9, 10 for the rolling bodies 5, obtained on an inner lateral surface of the outer ring 3 and on an outer lateral surface of the inner ring 4, respectively, to one or more of the rolling bodies 5, or to more than one of these possibilities combined together. Such defects, usually of the superficial type (abrasions, scratches, etc.) actually cause impacts when the rolling bodies 5 roll on tracks 9, 10; such impacts are the cause for the abnormal noisiness and vibrations.

As is known, noise is just an acoustic expression of a vibration. Vibrations also occur in a bearing 2b or 2c free from defects due to the relative rotation of the various components, and a vibration thus occurs and a noise is emitted, which however remains at low levels and is substantially inaudible. Such vibrations are related to the bearing geometry and since they are vibrations caused by a rotation, they are defined by periodical functions, either simple (e.g. sinusoidal) or complex (e.g. overlapping, dampened sinusoidal functions); the vibration frequencies of the various members, typically inner ring 4, outer ring 3, rolling bodies 5 and train of rolling bodies 5 (bearing 2c) forming a crown of rolling bodies, may be calculated with suitable mathematical models, known to those skilled in the art, once the relative rotation speed between rings 3 and 4 has been fixed.

The Applicant's experts have proved that in the presence of defects and thus of abnormal noisiness and vibrations of bearing 2b/2c, the bearing has different specific vibration frequencies that are correlated with the different types of defects and which may be predicted according to the following formulas:

$$f_{ord} = l * z * f_c \quad (1)$$

$$f_{ird} = l * z * (f_i - f_c) \pm n * f_i \quad (2)$$

$$f_{bd} = 2 * l * f_\omega \quad (3)$$

where:
$f_{ord}$=vibration frequency for a defect on ring 3;
$f_{ird}$=vibration frequency for a defect on ring 4;
$f_{bd}$=vibration frequency for a defect on rolling body 5;
$f_c$=rotation frequency of the train of rolling bodies 5;
$f_i$=rotation frequency of the inner ring 4;
$f_\omega$=rotation frequency of the rolling bodies 5 (balls) about their center;
l, n=any positive integer;
z=number of rolling bodies 5 present.

Therefore, according to the invention, noisiness and abnormal vibrations of a bearing 2b/2c related to a surface defect of one or more components thereof (3, 4 or 5 in the case of bearing 2c) may be detected according to the analysis of the vibration frequencies of bearing 2 at a known speed, which is fixed in advance according to the average rotation speed to which bearing 2 is subjected in operation, for example, at the vehicle speeds at which noisiness and abnormal vibration more frequently occur.

To this end, apparatus 1 comprises a base 11, preferably mounted to pivoting wheels 12, so as to easily move the whole apparatus 1.

Apparatus 1 further comprises a first support 13 carried by base 11; support 13 in turn comprises a slide 14 slidingly carried by base 11 in a predetermined direction D (FIG. 5); and a group 15 of fixtures 37 and 46 (described in detail hereafter) adapted to integrally receive in use the outer ring 3 which, in the examples shown, is also that intended to remain stationary in use. The group 15 of fixtures 37 and 46 is easily removably and selectively carried by slide 14, so that slide 14 receives in use the two fixtures 37 and 46 only one at a time; moreover, fixtures 37 and 46 are shaped and positioned on slide 14 so that the axis of symmetry A of the ring (specifically, ring 3) integrally supported by them is arranged parallel to the predetermined sliding direction D of slide 14.

According to the invention, apparatus 1 comprises a first accelerometer 16 and a second accelerometer 17 accommodated in respective seats 18 (FIGS. 3 and 4) provided on support 13, so that respective measurement axes X and Y of accelerometers 16, 17, respectively, are arranged at an angle α relative to each other which preferably forms a right angle, on a plane perpendicular to the axis of symmetry A of bearing 2b/2c, coincident with the sheet plane in FIGS. 3 and 4.

Accelerometers 16, 17 are of any known type, e.g. of the piezoelectric type with a movable mass. Apparatus 1 further comprises a mechanical system 19 (described in detail hereafter) for rotating the inner ring 4 at a predetermined speed, which in these two non-limiting examples shown is the one intended, in use, to be the relatively movable ring of bearing 2b or 2c.

In order to carry out measurements on bearings 2b, 2c with two crowns of rolling bodies (the bearings constituting wheel hub units may have two crowns of balls or two crowns of rollers, or even mixed crowns), apparatus 1 is also provided with a mechanical device 20 for axially moving slide 14 along the predetermined direction D and for selectively applying, by means of slide 14 and to the ring 3 integral with support 13, a first and a second axial thrust S1, S2 (FIG. 5) parallel to the axis of symmetry A of rings 3, 4 and in opposite directions.

Apparatus 1 finally comprises data processing means 21, of any known type and diagrammatically shown with a block in FIG. 2, for processing a first and a second electric signal T1 and T2, respectively (FIG. 2), emitted by the first and the second accelerometers 16, 17, respectively, which signals reach the processing means 21 through a data line 22.

The processing means 21 may consist of a simple portable computer provided with statistical analysis software and with an interface card for the connection with accelerometers 16, 17.

Slide 14 is movably mounted along respective rectilinear guides 23 integrally carried by base 11 in a known manner. In particular, slide 14 is constrained to the guides 23 by means of a runner 24 underneath the slide 14 and which slidingly engages, substantially without clearance, the guides 23; runner 24 is connected with slide 14 by means of blocks 25 which preferably are all of the vibration damper type, and is connected to an actuator 49 (FIGS. 1 and 5).

The rotation system 19 for the inner ring 4 comprises an electric motor 26 carried by base 11, a second support 27 carried in fixed position by base 11 in front of support 13 and which idly and overhangly supports an annular driven element 28, so that the driven element 28 is in use coaxial with the axis of symmetry A of rings 3, 4 of bearing 2; and means 29 of the known type for transmitting the motion from motor 19 to the driven element 28, defined for example by a flat belt (shown with a dashed line), which on the one hand engages the driven element 28 and on the other hand a pulley 30 (FIG. 1) of motor 26.

The driven element 28 comprises a guiding element 32 (FIG. 5) for angularly integrally engaging ring 4; moreover, support 27 is crossed by an axial hole 31 arranged in use coaxial to the axis of symmetry A of the rings 3, 4 of bearing 2.

If the subject bearing is free from flange 7, the guiding element 32 comprises an annular prong 33 (FIG. 5), which extends axially overhangly from the second support 27 and from the driven element 28, to which it is fixed by means of screws; in the example shown, prong 33 is adapted to angularly integrally receive the inner ring of bearing 2b in axial abutment towards support 27, and serves the function of axle.

Vice versa, in the case of bearing 2c, in which ring 4 is provided with flange 7, the guiding element 32 comprises a ring 34 (FIG. 7) which extends axially overhangly from the second support 27 and which is peripherally provided with seats 35 for angularly integrally receiving the fastening means 8.

According to an aspect of the invention, prong 33 and ring 34 can be selectively mounted integral with the driven element 28 into the same reception seat 36 carried by the driven element 28 (FIG. 5).

If the outer ring is free from flange (the case of bearing 2b), the group 15 of fixtures comprises a first fixture 37 (FIGS. 1, 3 and 5), in turn comprising at least one pair of annular or semi-annular movable jaws 38, adapted to axially sandwich the outer ring on opposite sides and carried by a holder 39 for the jaws 38 which is removably fixable to slide 14, at a reception seat 40 of slide 14.

If the inner ring is free from flange (bearing 2b), apparatus 1 comprises a third support 41 (FIGS. 1 and 5) arranged, with respect to the second support 27, on the side opposite that facing the first support 13, and which overhangly and idly carries a shaft 42 which is thoroughly inserted into the axial hole 31 of the second support 27 and through the driven element 28; shaft 42 is axially movable and is provided, at an internally hollow free end 43 thereof, with tilting shoulder means 44 adapted to be coupled to the edge of the inner ring 4; support 41 carries a linear actuator 45 acting on shaft 42 for moving in use the shoulder means 44 against an edge of ring 4 and thereby axially locking ring 4, further applying a predetermined axial thrust to tracks 10.

When ring 4 is provided with flange 7 (which generally only occurs in bearings 2c constituting third-generation wheel hub units, provided with both flanges 6, 7 and in which tracks 10 are subjected to an axial preload), support 41 with shaft 42 and accessories 45 and 44 are removed from apparatus 1 as they are unnecessary.

If ring 3 is provided with flange 6 (bearing 2c), the group of fixtures 15 comprises a second fixture 46 (FIGS. 2 and 4), alternative to fixture 37, consisting of at least one saddle-shaped bracket 47 connectable to flange 6; bracket 47 is provided with seats 48 (FIG. 4) for receiving removable fixing means (such as screws or bolts, known and not shown) to flange 6, and is removably fixable to slide 14 at the same reception seat 40 of slide 14 for the holder 39 of the jaws 38 of fixture 37.

Therefore, according to an aspect of the invention, fixtures 37 and 46 are selectively mountable one at a time to slide 14, as already mentioned above.

Finally, seats 18 for accelerometers 16, 17 are obtained both directly on slide 14, and in jaws 38 with reference to fixture 37 (FIG. 3) and in bracket 47 with reference to fixture 46 (FIG. 4), so that accelerometers 16, 17 may be mounted both directly to slide 14 and to fixtures 37, 46.

Due to the above-described apparatus 1, a method for measuring the noisiness and vibrations generated by a bearing, in particular constituting a wheel hub unit as described above, may be carried out on a bearing of any type, e.g. of first generation (bearing 2b), free from flanges 6 and 7, of second generation, provided with flange 6 only, and of third generation, provided with both flanges 6 and 7, so as to easily detect the generation of abnormal noisiness and vibrations, indicating a defect present in the bearing itself.

Figure 6:
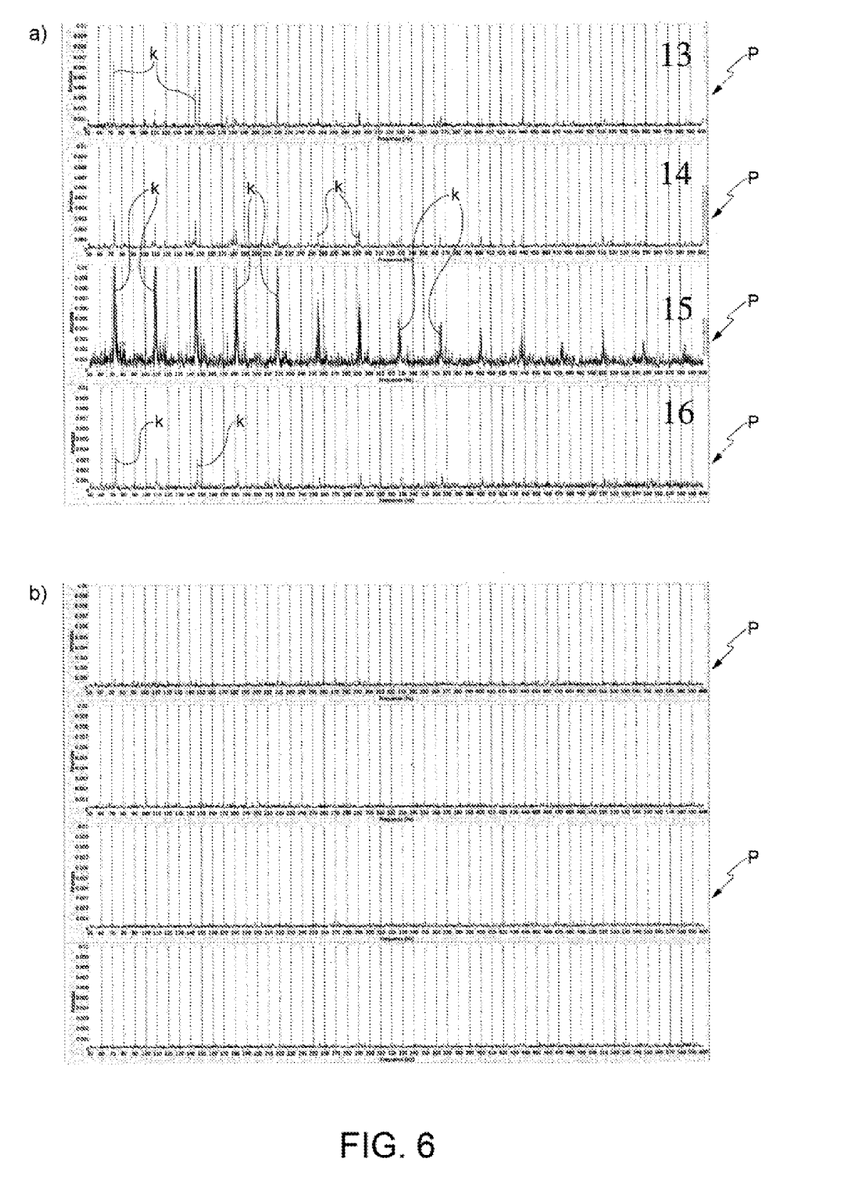
FIG. 6 qualitatively shows two graphs which can be obtained by means of the measurement method of the invention, referred to a group of non-defective bearings/wheel hub units (FIG. 6b) and to a group of defective bearings/wheel hub units (FIG. 6a)

The measurement method according to the invention comprises the steps of:

a)—mounting the outer ring 3, specifically the one intended to remain stationary in use, integral to support 13 which is provided with accelerometers 16, 17 so that accelerometers 16, 17 have respective measurement axes X, Y arranged at a right angle relative to each other on a plane perpendicular to the axis of symmetry A of bearing 2;

b)—rotating, through the means 19, the inner ring 4, specifically the one intended to be in use the relatively movable ring, at a predetermined speed, calculated beforehand based on operating parameters of the bearing in use, typically the average relative rotation speed between rings 3, 4 at the speeds at which possible abnormal noisiness and vibrations usually develop on the vehicle; such speed is preferably assumed as equal to 1000 RPM;

c)—detecting the first and second electric signals T1, T2 in a first predetermined time interval (such as few seconds), which signals are emitted by the first and second accelerometers 16, 17, respectively; according to the above description, such signals T1 and T2 are proportional to the variation along time of a magnitude of a first and a second vector component, arranged along axes X and Y or in any case parallel thereto, of possible vibrations of the support 13, which vibrations can be generated on support 13, due to the presence of the vibration damper blocks 25, only through transmission by bearing 2;

d)—processing the first and second electric signals T1, T2 through the means 21 for obtaining a frequency spectrum P (FIG. 6) of the possible vibrations detected (and noisiness, accordingly), so as to obtain a diagram as those shown in FIG. 6a and identified by the sequence numbers P13, P14, P15 and P16, which in modulus represents the amplitude of any vibrations detected compared to the frequency of any vibrations detected; and e)—determining that bearing 2 has abnormal noisiness or vibrations as a consequence of at least one defect present in bearing 2, if such a diagram has amplitude levels higher than a threshold at predetermined frequency intervals represented by peaks in amplitude K (frequency spectra represented by graphs P13 to P16 in FIG. 6a).

In particular, the processing step d) comprises the steps of:
    interpolating the absolute values of the first and second electric signals T1, T2 so as to calculate in modulus a variation of a vibration amplitude vector as a function of time;

transforming, e.g. by using a Fourier transform, the calculated vector into a frequency spectrum P which provides the variation of the vibration amplitude vector as a function of the vibration frequencies detected.

The predetermined frequency intervals at which peaks in amplitude K may appear in the graphs representing the frequency spectra P in the presence of defects are calculated beforehand using the above-shown mathematical formulas (1), (2) and (3), adding a fixed value, such as ±2 Hz, to the calculated values $f_{ord}$ (vibration frequency for a defect on ring 3), $f_{ird}$ (vibration frequency for a defect on ring 4) and $f_{bd}$ (vibration frequency for a defect on rolling body 5).

If the rotation speed of motor 26 is electronically controlled and may be deemed as perfectly constant, such intervals may have an amplitude close to zero and peaks K occur exactly at the frequencies estimated in the calculation.

As seen, formulas (1), (2) and (3) are based on the analysis of the construction parameters of bearing 2, which provide the "natural" vibration frequencies $f_c$, $f_i$ and $f_\omega$ of the various components of bearings 2 free from defects.

The method according to the invention further comprises the step of associating the abnormal noisiness and vibrations detected according to the presence of more or less accentuated peaks in amplitude K with one or more specific defects of the bearing (multiple different defects may be present on the same bearing at the same time), which are determined according to the frequency values associated with the detected peaks.

In essence, if a spectrum P has peaks K at frequencies $f_{ord}$, there will be a defect on one of the tracks 9 of ring 3, if it has them at the frequencies $f_{ird}$ there will be a defect on the tracks 10 of ring 4, and finally if it has them at the frequencies $f_{bd}$ there will be a defect on the rolling bodies 5. According to the above description, multiple peaks at different frequencies may be present at the same time, indicating the concurrent presence of defects of different type.

By comparison, FIG. 6b shows spectra P obtainable from bearings 2 free from defects; as may be seen, peaks K are absent.

Finally, when bearing 2 has two crowns of rolling bodies, as in the case of bearings 2 intended for wheel assemblies of vehicles or constituting wheel hub units, steps b) and c) are carried out by selectively applying the axial thrusts S1 and S2 on support 13, which thrusts are parallel to the axis of symmetry A and in opposite direction, so as to put only one track 9 at a time under load, i.e. the one associated with the crown of rolling bodies 5 arranged in use towards the interior of the vehicle, and the one associated with the crown of rolling bodies 5 arranged in use towards the exterior of the vehicle, respectively, thus allowing the noisiness and vibrations associated with defects present at each crown of rolling bodies to be selectively detected.

In essence, six frequency spectra P will be finally generated for each bearing 2 examined.

The above-described method is clearly simple to be implemented and highly accurate and does not require any disassembly operation to be carried out on bearings 2.

The invention claimed is:

1. An apparatus for measurement of the noisiness and of the vibrations of a rolling bearing having an outer ring and an inner ring mounted coaxial to each other with respect to an axis of symmetry (A) and between at least one crown of rolling bodies, comprising:
    a base;
    a first support supported by the base and having a slide slidingly supported by the base in a predetermined direction (D) and means removably supported by the slide, adapted to integrally receive a first one of the outer ring and the inner ring of the bearing, with the axis of symmetry (A) arranged parallel to the predetermined sliding direction (D) of the slide;
    a first and a second accelerometer accommodated into respective seats provided on the first support so that respective measurement axes (X, Y) of the accelerometers are arranged at a right angle relative to each other on a plane perpendicular to the axis of symmetry of the bearing;
    means for rotating at a predetermined speed a second one of the outer ring and the inner ring of the bearing;
    means for axially moving the slide along the predetermined direction (D) and for selectively applying, by the slide, a first and a second axial thrust (S1, S2) parallel to the axis of symmetry (A) of the inner and outer ring and with opposite direction, to the first one of the outer ring and the inner ring that is integral to the first support; and
    data processing means for processing a first and a second electric signal (T1, T2) emitted by the first and the second accelerometer, respectively,
    wherein the means for rotating at the predetermined speed the second one of the outer ring and the inner ring includes an electric motor supported by the base, a second support supported in fixed position by the base in front of the first support and idly supports an annular driven element so that the annular driven element is coaxial to the axis of symmetry (A) of the bearing rings, the annular driven element having means for angularly integrally engaging the second one of the outer ring and the inner ring and motion transmission means from the electric motor to the annular driven element; the second support being crossed by an axial hole arranged coaxial to the axis of symmetry (A) of the bearing rings,
    wherein the means for angularly integrally engaging the second one of the outer ring and the inner ring includes an annular prong that axially overhangly extends from the second support and from the annular driven element and is adapted to angularly integrally receive the second one of the outer ring and the inner ring; and a ring that axially overhangly extends from the second support that is peripherally provided with seats for angularly integrally receiving fastening means of a flange of the second one of the outer ring and the inner ring; the annular prong and the ring being selectively mountable integral to the annular driven element, one at a time, into a same reception seat of the driven element.

2. The apparatus according to claim 1, wherein the slide is movably mounted along respective rectilinear guides integrally supported by the base, which guides are engaged by a runner underneath the slide; the runner being connected to the slide by means of vibration damper blocks.

3. An apparatus for measurement of the noisiness and of the vibrations of a rolling bearing having an outer ring and an inner ring mounted coaxial to each other with respect to an axis of symmetry (A) and between at least one crown of rolling bodies, comprising:
    a base;
    a first support supported by the base and having a slide slidingly supported by the base in a predetermined direction (D) and means removably supported by the slide, adapted to integrally receive a first one of the outer ring and the inner ring of the bearing, with the axis of symmetry (A) arranged parallel to the predetermined sliding direction (D) of the slide;

a first and a second accelerometer accommodated into respective seats provided on the first support so that respective measurement axes (X, Y) of the accelerometers are arranged at a right angle relative to each other on a plane perpendicular to the axis of symmetry of the bearing;

means for rotating at a predetermined speed a second one of the outer ring and the inner ring of the bearing;

means for axially moving the slide along the predetermined direction (D) and for selectively applying, by the slide, a first and a second axial thrust (S1, S2) parallel to the axis of symmetry (A) of the inner and outer ring and with opposite direction, to the first one of the outer ring and the inner ring that is integral to the first support; and data processing means for processing a first and a second electric signal (T1, T2) emitted by the first and the second accelerometer, respectively, wherein the slide is movably mounted along respective rectilinear guides integrally supported by the base, which guides are engaged by a runner underneath the slide; the runner being connected to the slide by means of vibration damper blocks, wherein the means removably supported by the slide and adapted to integrally receive the first one of the outer ring and the inner ring provides a first fixture comprising:

at least one pair of annular or semi-annular movable jaws adapted to axially clamp the first one of the outer ring and the inner ring on opposing sides and carried by a jaw holder removably fixable to the slide at a reception seat of the slide;

a second support supported in fixed position by the base in front of the first support and idly supports an annular driven element so that the annular driven element is coaxial to the axis of symmetry (A) of the bearing rings; and a third support arranged, with respect to the second support, on the side opposite that facing the first support and which overhangly and idly carries a shaft that thoroughly inserts into an axial hole of the second support and through the annular driven element; the shaft being axially movable and being provided, at a free end thereof, with tilting shoulder means adapted to couple with the second one of the outer ring and the inner ring; the third support carrying an actuator acting on the shaft for applying, by means of the tilting shoulder means, an axial thrust to the second one of the outer ring and the inner ring.

4. The apparatus according to claim 3, wherein the means removably supported by the slide and adapted to integrally receive the first one of the outer ring and the inner ring of the bearing provides a second fixture consisting in at least one saddle shaped bracket and connectable with a flange of the first one of the outer ring and the inner ring, the at least one saddle shaped bracket being provided with seats for receiving removable holding means to the flange and being removably fixable to the slide at the same reception seat of the slide for the holder for the jaws of the first fixture, the first and second fixture being selectively mountable one at a time on the slide and with reference to the third support, on the base.

5. A method for measurement of the noisiness and of the vibrations of a rolling bearing in a wheel hub bearing unit, having an outer ring and an inner ring mounted coaxial to each other with respect to an axis of symmetry (A) and between at least one crown of rolling bodies, comprising the steps of:

providing an apparatus comprising:
a base;
a first support supported by the base and having a slide slidingly supported by the base in a predetermined direction (D) and means removably supported by the slide, adapted to integrally receive the outer ring of the rolling bearing, with the axis of symmetry (A) arranged parallel to the predetermined sliding direction (D) of the slide;

a first and a second accelerometer accommodated into respective seats provided on the first support so that respective measurement axes (X, Y) of the accelerometers are arranged at a right angle relative to each other on a plane perpendicular to the axis of symmetry of the rolling bearing;

means for rotating at a predetermined speed the inner ring of the rolling bearing;

means for axially moving the slide along the predetermined direction (D) and for selectively applying, by the slide, a first and a second axial thrust (S1, S2) parallel to the axis of symmetry (A) of the inner and outer ring and with opposite direction, to the outer ring that is integral to the first support;

wherein the means for rotating at the predetermined speed the inner ring includes an electric motor supported by the base, a second support supported in fixed position by the base in front of the first support and idly supports an annular driven element so that the annular driven element is coaxial to the axis of symmetry (A) of the bearing rings, the annular driven element having means for angularly integrally engaging the inner ring and motion transmission means from the electric motor to the annular driven element; the second support being crossed by an axial hole arranged coaxial to the axis of symmetry (A) of the bearing rings, wherein the means for angularly integrally engaging the inner ring includes an annular prong that axially overhangly extends from the second support and from the annular driven element and is adapted to angularly integrally receive the inner ring; and a ring that axially overhangly extends from the second support that is peripherally provided with seats for angularly integrally receiving fastening means of a flange of the inner ring; the annular prong and the ring being selectively mountable integral to the annular driven element, one at a time, into a same reception seat of the driven element;

mounting the outer ring integrally to the first support;

rotating the inner ring, at the predetermined speed, calculated beforehand based on operating parameters of the rolling bearing;

detecting a first and a second electric signal (T1, T2) in a first predetermined time interval, respectively emitted by the first and second accelerometer which are proportional to the variation along time of a magnitude of a first and a second vector component of possible support vibrations, which components are parallel to the measurement axes (X, Y) of the accelerometers;

processing the first and the second electric signal (T1, T2) for obtaining a spectrum in frequency (P) of the amplitude of the possible vibrations detected, to obtain a diagram (P13-P16) that in modulus represents the amplitude of any vibrations detected versus the frequency of any vibrations detected, respectively; and determining that the rolling bearing has abnormal noisiness and vibrations consequence of at least one defect present in the rolling bearing if the diagram has peaks (K) of amplitude levels at predetermined frequency intervals.

6. The method according to claim 5, wherein the processing step further comprises the steps of:

interpolating the absolute values of the first and second electric signal (T1, T2) to calculate in modulus a variation of a vibration amplitude vector as function of time;

transforming using a Fourier transform, the calculated vector into a spectrum in frequency (P) that provides the variation of the vibration amplitude vector as function of the vibration frequencies detected.

7. The method according to claim 5, wherein the predetermined frequency intervals at which the peaks (K) of amplitude levels may appear in the diagram in the presence of one or more defects are calculated beforehand, based on mathematical formulas based on construction parameters of the bearing which provide the vibration frequencies of defect-free bearings.

8. The method according to claim 5, wherein the step of associating the abnormal noisiness and vibrations detected with one or more specific defects of the bearing, which are determined based on the frequency values associated with the detected peaks in amplitude (K).

9. The method according to claim 5, wherein the rolling bearing has two crowns of rolling bodies, steps of rotating the inner ring and detecting the first and the second electric signal are carried out by selectively applying a first and a second axial thrust (S1, S2) on the first support, parallel to the axis of symmetry of the inner and outer ring and with opposite direction, to selectively detect the noisiness and vibrations associated with defects present at each crown of rolling bodies.

\* \* \* \* \*